United States Patent
Ito et al.

(10) Patent No.: US 8,530,714 B2
(45) Date of Patent: Sep. 10, 2013

(54) METHOD FOR PRODUCTION OF LOWER OLEFIN

(75) Inventors: Hirofumi Ito, Higashiibaraki-gun (JP); Kazunori Honda, Higashiibaraki-gun (JP); Koji Oyama, Yokohama (JP); Nobuyasu Chikamatsu, Yokohama (JP); Kazutaka Hiraoka, Higashiibaraki-gun (JP); Atsushi Okita, Higashiibaraki-gun (JP)

(73) Assignee: JGC Corporation, Tokyo (JP)

( * ) Notice: Subject to any disclaimer, the term of this patent is extended or adjusted under 35 U.S.C. 154(b) by 918 days.

(21) Appl. No.: 12/085,055

(22) PCT Filed: Nov. 13, 2006

(86) PCT No.: PCT/JP2006/322577
§ 371 (c)(1),
(2), (4) Date: May 14, 2008

(87) PCT Pub. No.: WO2007/055357
PCT Pub. Date: May 18, 2007

(65) Prior Publication Data
US 2010/0217054 A1  Aug. 26, 2010

(30) Foreign Application Priority Data

Nov. 14, 2005 (JP) ................................. 2005-329106
Sep. 22, 2006 (JP) ................................. 2006-257708

(51) Int. Cl.
*C07C 1/20* (2006.01)
(52) U.S. Cl.
USPC ........... 585/640; 585/301; 585/302; 585/638; 585/639
(58) Field of Classification Search
USPC ................. 585/300, 324, 408, 469, 639, 640, 585/733, 301, 638, 302
See application file for complete search history.

(56) References Cited

U.S. PATENT DOCUMENTS 4,083,888 A   4/1978 Caesar et al.
4,550,217 A * 10/1985 Graziani et al. ............. 585/324

(Continued)

FOREIGN PATENT DOCUMENTS

DE   3524890 A1   1/1986
DE   10027159 A1  12/2001

(Continued)

OTHER PUBLICATIONS

Chang et al., "The Conversion of Methanol and Other O-Compounds to Hydrocarbons over Zeolite Catalysts", Journal of Catalysis, vol. 56, pp. 169-174, 1979.
Berry et al., Chem. Eng., 1980 (8), 87 (A drawing only).

*Primary Examiner* — In Suk Bullock
*Assistant Examiner* — Bradley Etherton
(74) *Attorney, Agent, or Firm* — The Webb Law Firm

(57) ABSTRACT

Disclosed is a method for production of lower olefins from a raw material containing dimethyl ether (DME), which can produce lower olefins (e.g. propylene) with good yield and in an economically advantageous manner by prolonging the time until the reversible deactivation of a zeolite catalyst and preventing the irreversible deactivation of the catalyst, can reduce the amount of water to be recycled to increase the thermal efficiency of the process, and can simplify the facilities and operations. Also disclosed is a method for improving the yield of propylene with good efficiency under practical operating conditions. A feed gas which comprises a DME-containing feedstock gas and an additive gas and further contains steam at a specific proportion is introduced into an olefin synthesis reactor to contact the feed gas with a zeolite catalyst, thereby producing a hydrocarbon product containing C2-C5 olefins. Propylene or the like is separated/collected from the hydrocarbon product, and at least a part of the remainder is used as at least a part of the additive gas.

6 Claims, 8 Drawing Sheets

(56) References Cited

U.S. PATENT DOCUMENTS

| | | | |
|---|---|---|---|
| 5,744,680 A * | 4/1998 | Mulvaney et al. | 585/640 |
| 6,399,844 B1 * | 6/2002 | van Dijk | 585/639 |
| 6,433,239 B1 * | 8/2002 | VanDijk | 585/640 |
| 7,015,369 B2 | 3/2006 | Hack et al. | |
| 7,102,050 B1 * | 9/2006 | Lattner et al. | 585/640 |
| 2002/0063240 A1 * | 5/2002 | Munson et al. | 252/184 |
| 2003/0139635 A1 * | 7/2003 | Hack et al. | 585/609 |
| 2006/0229482 A1 * | 10/2006 | Setoyama et al. | 585/638 |
| 2007/0027351 A1 * | 2/2007 | Dath et al. | 585/639 |

FOREIGN PATENT DOCUMENTS

| | | |
|---|---|---|
| JP | 4217928 | 8/1992 |
| JP | 2005104912 | 4/2005 |
| JP | 2005232121 | 9/2005 |
| WO | 9915482 A1 | 4/1999 |
| WO | 0192190 | 12/2001 |
| WO | 0210098 A1 | 2/2002 |
| WO | WO 2005056504 A1 * | 6/2005 |

\* cited by examiner

METHOD FOR PRODUCTION OF LOWER OLEFIN

The present application claims priority from Japanese Patent Application No. 2005-329106 and Japanese Patent Application No. 2006-257708, which are hereby incorporated by reference.

TECHNICAL FIELD

The present invention relates to a method for producing lower olefins such as propylene and the like from a feedstock gas containing dimethyl ether. More particularly, the present invention relates to a method for producing lower olefins from a feedstock gas containing dimethyl ether using a catalyst, whereby propylene is produced with a high yield.

BACKGROUND ART

Conventionally, there has been known a method in which dimethyl ether or a mixture of dimethyl ether and methanol is subjected to dehydration reaction by bringing into contact with a zeolite catalyst to convert into lower olefins containing ethylene and propylene.

This method has a problem that, although the dehydration reaction is continuously carried out while a feedstock gas containing dimethyl ether is fed to zeolite, the zeolite catalyst is gradually deactivated (reversible deactivation) because deposited carbonaceous deposits adhere to the pore surface of the zeolite with time and the active sites which effectively act on the reaction are poisoned. Therefore, it is required to repeat the operation of regenerating the deactivated zeolite catalyst to recover the activity.

For this reason, it has been studied to improve the life of a zeolite catalyst by suppressing the deterioration of the catalyst activity with time from the aspect of the production efficiency and cost of the lower olefin.

Here, the problematic deactivation includes a irreversible deactivation as described later other than the above-mentioned reversible deactivation. The reversible deactivation is poisoning of a catalyst active site caused by the accumulation of carbonaceous deposits, which may be regenerated by burning in air. On the one hand, the irreversible deactivation is the disappearance of the active site due to aluminum removal caused by exposure to steam and heat and may not be regenerated because of the irreversible structural change.

In producing lower olefins from methanol and dimethyl ether (DME) in the presence of a zeolite catalyst, it is considered that the reaction sequentially proceeds by the following pathway to form carbonaceous deposits.

Methanol→Dimethyl ether→Olefin→Aromatic Compound→Carbonaceous Deposits

In order to suppress the formation of carbonaceous deposits caused by this reaction and to suppress the deterioration of a catalyst caused by heat damage, the excessive temperature rise of a catalyst bed is preferably prevented and the removal of the heat of reaction is effective. In addition, the removal of the reaction heat is critical from the viewpoint of safe operation of equipment. For this reason, various methods have been proposed in order to reduce the temperature rise of the catalyst bed.

For example, there has been adopted a method in which, before a feedstock gas is introduced into a reactor producing lower olefins, the reaction is divided into two stages by providing a reactor which converts methanol to dimethyl ether in advance, thereby reducing the temperature rise of the catalyst bed. In addition, there has been adopted a method in which a dilution gas is added into the feedstock gas to reduce the temperature rise. For example, in Patent Document 1, there is shown an example in which, as a dilution gas, hydrogen, helium, nitrogen, carbon dioxide or $C_1$-$C_7$ saturated hydrocarbons are added two to 20 times the amount of the methanol raw material.

It is known that, if the partial pressure of a feedstock gas is reduced by diluting the feedstock gas, the temperature rise of the catalyst bed may not only be suppressed but also the resulting olefin may be prevented to sequentially react, thereby sometimes contributing to the yield improvement of the lower olefin. Therefore, there is widely adopted a method of using a large amount of steam as a dilution gas. In a commercial process, a separation process is required to be provided at a later stage of an olefin synthesis reactor. Steam is more easily separated than other dilution gases, and water is produced as a by-product by the dehydration reaction of the feedstock gas and may be recycled for reuse, which is also a reason for requesting the use of steam as a dilution gas. For example, in Patent Document 2, it is described that lower olefins are produced by setting the partial pressure of steam in the feed to 40 to 80% by volume.

However, although the formation of carbonaceous deposits is alleviated and the time to the reversible deactivation of a zeolite catalyst is extended by the addition of steam in a high concentration, there exists a problem that sufficient catalyst activity and life cannot be obtained after regeneration. It is considered that the skeletal aluminum that forms an active site of a catalyst is extracted from the zeolite framework structure in the presence of steam, causing irreproducible deactivation (irreversible deactivation).

Moreover, when steam is further added as a dilution gas in addition to the steam generated by the reactor for converting methanol into dimethyl ether installed at the earlier stage of a reactor for producing lower olefins as mentioned above, a great deal of evaporation energy is required to generate steam, thus decreasing the thermal efficiency of the whole process. Furthermore, since steam generation equipment is required, the equipment configuration becomes complex, raising the cost of process construction. The production method has also a problem that the operation of the equipment becomes complex.

Furthermore, as another method of suppressing the reversible deactivation of a catalyst caused by the formation of carbonaceous deposits, improvement of a catalyst has been studied. For example, there is known a method in which the density of the active site on a catalyst is decreased by increasing the ratio of Si to Al in ZSM-5 or by supporting a basic metal to poison a part of acid sites.

However, even though any of these methods is adopted, it may not prevent the activity deterioration (reversible deactivation) caused by the formation of carbonaceous deposits on the catalyst with time and the catalyst is required to be regenerated by combustion to remove carbon at a fixed interval.

As a technique aiming at prolonging the regeneration cycle of a catalyst, the present applicants have already proposed a method of reducing the amount of accumulated carbon by the addition of carbon dioxide in a feedstock gas containing dimethyl ether (refer to Patent Document 3). It is considered that this method reduces the accumulation of carbonaceous deposits on the catalyst by gasification of the precipitated carbonaceous deposits by carbon dioxide gas. Although this method reduces the formation of carbonaceous deposits on the catalyst without accelerating the irreversible deactivation and accomplishes the prolongation of the regeneration cycle of a catalyst, further technical improvement has been desired.

Under these circumstances, it has been strongly desired to realize a method for producing lower olefins from a raw material containing dimethyl ether, which may extend the time to the reversible deactivation of a zeolite catalyst by suppressing the formation of carbonaceous deposits on the catalyst, may maintain sufficient activity of the catalyst after regeneration for a prolonged period of time with less irreversible deactivation of the catalyst and may produce lower olefins, propylene in particular, with a high yield at a low cost.

In addition, on the other hand, since a great deal of heat generation is accompanied by the reaction of producing lower olefins such as propylene, ethylene and the like from dimethyl ether or methanol by using a catalyst, heat control becomes an important problem from the viewpoint of suppressing the deterioration of a catalyst and the damage caused by heat in constructing a reactor and moreover from the viewpoint of safe operation of the reactor. For this reason, there have been proposed various methods for reducing the temperature rise of a catalyst bed.

For example, in Patent Document 1, there is described a method of distributing heat generation by installing a reactor which converts methanol into dimethyl ether ahead of a hydrocarbon-production reactor. In addition, in Patent Document 4, there is described a method of reducing temperature rise by adding a dilution gas into a feedstock gas. Further, in a production process of lower olefins using a SAPO-34 catalyst, which is a different type of catalyst, fluidized-bed reactor has been used as heat control.

Since the amount of generated heat due to the reaction is proportional to the feed amount of a raw material, it is also effective for the reduction of temperature rise of the catalyst bed to divide feeding of a raw material by dividing a reactor into multiple stages. In Patent Document 5, there is proposed a method in which multiple reactors are used in series and a raw material is divided and fed into each reactor to be reacted in multiple stages, and it is described that the yield of propylene may be increased without using a costly tubular reactor. This method is expected to alleviate the temperature rise per one reactor by using at least two shaft reactors.

Although the reason why the propylene yield is increased is not specifically described in Patent Document 5, in the method described in Patent Document 5, the increase in the propylene yield is considered to be accomplished by reducing the partial pressure of a raw material. When using multiple reactors, parallel installation of the rectors is effective for the reduction of the temperature rise, but the propylene yield in the resulting lower olefin is expected to increase more when the reactors are installed in series because the partial pressure of the raw material in each reactor may be reduced. It is considered that this is attributed to the suppression of consecutive reaction of the resulting lower olefin to aromatics and the like by reducing the partial pressure of the raw material in producing propylene from dimethyl ether as reported in Non-Patent Document 2, for example.

However, the present inventors have obtained and analyzed data using a test apparatus capable of simulating practical operating conditions. As a result, it was found that, under the practical operating conditions, the propylene yield was not sufficiently increased by only carrying out the reaction in multiple stages and reducing the partial pressure of the raw material by dividing the raw material in feeding. For this reason, it has been desired to realize a method for producing lower olefins further more effectively increasing the propylene yield.

Patent Document 1: U.S. Pat. No. 4,083,888
Patent Document 2: Japanese Published Patent Application No. 2003-535069
Patent Document 3: Japanese Laid-Open Patent Publication No. 2005-104912
Patent Document 4: U.S. Pat. No. 4,083,888
Patent Document 5: Japanese Published Patent Application No. 2003-535069
Non-Patent Document 1: Chemical Engineering, 1980 (8) 87.
Non-Patent Document 2: Journal of Catalysis, 56 (1979) 169.

An object of the present invention is to provide a method for producing lower olefins from a raw material containing dimethyl ether, which may produce the lower olefin, propylene in particular, economically and with a high yield by extending the time to the reversible deactivation of a zeolite catalyst by suppressing the formation of carbonaceous deposits on the catalyst and suppressing the irreversible deactivation of the catalyst, may reduce the amount of water to be recycled to increase the thermal efficiency of the process and may accomplish deletion or substantial scale reduction and simplification of operations of facilities related to the recycling of water and steam generation.

In addition, another object of the present invention is to provide a method for effectively improving the propylene yield under practical operating conditions, in the case of producing lower olefins from a feedstock gas containing dimethyl ether.

SUMMARY OF THE INVENTION

The first method for producing lower olefins of the present invention is characterized in that:

a feed gas composed of a feedstock gas containing dimethyl ether and an additive gas and containing steam in a ratio of 5 to 30% by volume of the total amount is introduced into an olefin synthesis reactor, the raw material is brought into contact with a zeolite catalyst in the reactor to produce a hydrocarbon product containing $C_2$-$C_5$ olefins, propylene and ethylene when needed are separated and recovered from the resulting hydrocarbon product, and at least a part of the remainder after separating propylene and ethylene when needed from the hydrocarbon product is used as at least a part of the additive gas.

In such a method for producing lower olefins of the present invention, it is preferable to use multiple reactors connected in series, in parallel or in combination thereof.

In a method for producing lower olefins of the present invention, the feedstock gas is preferably a gas containing dimethyl ether and methanol.

In a method for producing lower olefins of the present invention, the molar fraction (dimethyl ether:methanol) of dimethyl ether and methanol in the feedstock gas is preferably in the range of 6:0 to 6:5.

In a method for producing lower olefins of the present invention, it is preferable that the additive gas contain $C_4$ and/or $C_5$ olefins derived from the remainder after separating propylene and ethylene when needed from the hydrocarbon product, the ratio of the total amount of the $C_4$ and/or $C_5$ olefins in the additive gas to the total amount of methanol and dimethyl ether in the feedstock gas be 0.3 to 5.0 by molar ratio on a carbon basis, and the ratio of an additive gas excluding steam to a feedstock gas to be introduced into the olefin synthesis reactor (the number of moles of an additive gas excluding steam/the number of moles of a feedstock gas on a carbon basis) be in the range of 0.2 to 5.0.

In a method for producing lower olefins of the present invention, it is preferable that the zeolite catalyst have an MFI structure and it is also preferable that the atomic ratio of silicon to aluminum (Si/Al) in the zeolite catalyst be in the range of 50 to 300 by molar ratio, and furthermore, it is preferable that the zeolite catalyst contain an alkaline earth metal M and that an atomic ratio of the alkaline earth metal M to aluminum (M/Al) in the zeolite catalyst be 0.5 or more by molar ratio.

The second method for producing lower olefins of the present invention is characterized in that, under the conditions in which the space velocity represented by the feed rate of the total feedstock gas per hour to the total amount of the catalyst in all the olefin synthesis reactors is in the range of 0.5 to 50 $h^{-1}$ by WHSV on the basis of dimethyl ether:

a feedstock gas containing dimethyl ether is divided and fed into two or more olefin synthesis reactors connected in series, and the feedstock gas is brought into contact with a zeolite catalyst in the reactors to produce the lower olefin containing propylene.

In such a method for producing lower olefins of the present invention, the space velocity is preferably in the range of 1.0 to 10 $h^{-1}$.

In the method for producing lower olefins of the present invention, the feedstock gas preferably contains dimethyl ether and methanol.

In the method for producing lower olefins of the present invention, the additive gas is preferably introduced into the reaction system.

In the method for producing lower olefins of the present invention, the ratio of steam in the feed gas, which is the total of the feedstock gas and additive gas introduced into all the reactors is preferably in the range of 5 to 30% by volume.

In the method for producing lower olefins of the present invention, the additive gas preferably contains at least a part of the hydrocarbon which is the remainder after separating the lower olefin containing propylene from the product obtained from the olefin synthesis reactor at the most downstream.

In the method for producing lower olefins of the present invention, the additive gas preferably also contains at least a part of the hydrocarbon which is the remainder after separating the lower olefin containing propylene from the product obtained from an olefin producing unit, which produces olefins by thermal cracking and/or catalytic cracking of hydrocarbons.

In the method for producing lower olefins of the present invention, it is preferable that the additive gas be introduced only into the olefin synthesis reactor at the most upstream among the multiple olefin synthesis reactors connected in series.

In the method for producing lower olefins of the present invention, it is preferable that the zeolite catalyst have an MFI structure and it is also preferable that the atomic ratio of silicon to aluminum (Si/Al) in the zeolite catalyst be in the range of 50 to 300 by molar ratio, and furthermore, it is preferable that the zeolite catalyst contain an alkaline earth metal M and that the atomic ratio of the alkaline earth metal M to aluminum (M/Al) in the zeolite catalyst be 0.5 or more by molar ratio.

In addition, the method for producing lower olefins of the present invention is characterized in that, under the conditions in which the space velocity represented by the feed rate of the total feedstock gas per hour to the total amount of the catalyst in all the olefin synthesis reactors is in the range of 0.5 to 50 $h^{-1}$ by WHSV on the basis of dimethyl ether:

a feed gas composed of a feedstock gas containing dimethyl ether and an additive gas and containing steam in a ratio of 5 to 30% by volume in the total amount is divided and fed into two or more olefin synthesis reactors connected in series, the feedstock gas is brought into contact with a zeolite catalyst in the reactors, a hydrocarbon product containing $C_2$-$C_5$ olefins are produced, propylene and ethylene when needed are collected from the resulting hydrocarbon product, and at least a part of the remainder after separating propylene and ethylene when needed from the hydrocarbon product is used as at least a part of the additive gas.

According to the method for producing lower olefins of the present invention, the time to the reversible deactivation of a zeolite catalyst may be extended by suppressing the formation of carbonaceous deposits on the catalyst, the irreversible deactivation of the catalyst may be reduced, and the lower olefin may be produced from a raw material containing dimethyl ether with a high yield, economically and with high selectivity of propylene. Further, the method increases the thermal efficiency of the process by reducing the amount of water to be recycled and may accomplish deletion or substantial scale reduction and simplification of operations of facilities related to the recycling of water and steam generation.

In addition, according to the method for producing lower olefins of the present invention, the propylene yield may be increased efficiently by a convenient method even under practical operating conditions.

DETAILED DESCRIPTION OF THE INVENTION

Figure 1:
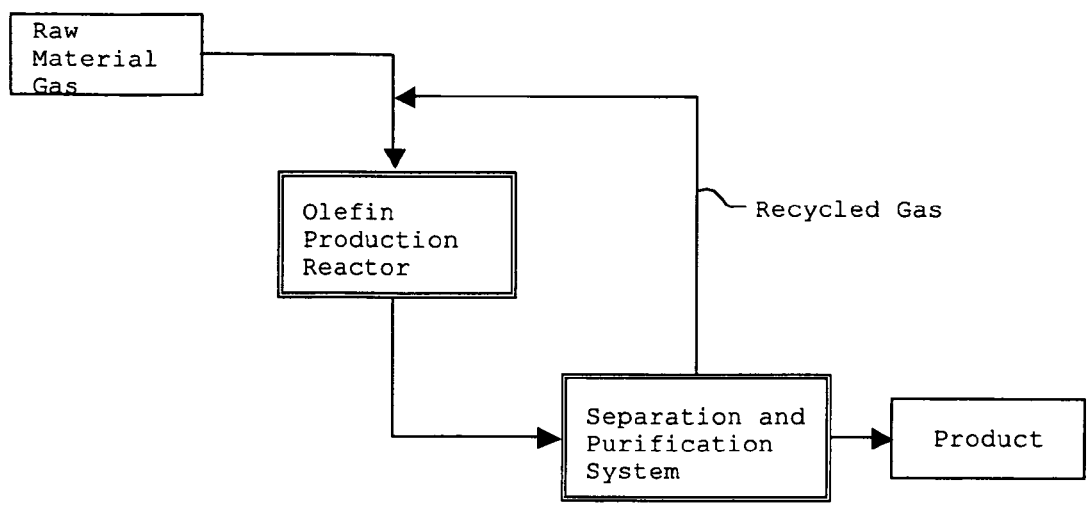
FIG. 1 is a schematic diagram showing an embodiment of the first invention in the case of using one olefin synthesis reactor.

Hereinafter, the present invention will be specifically explained.

The First Production Method of Lower Olefins

In the first method for producing lower olefins of the present invention, a feedstock gas containing dimethyl ether is brought into contact with a zeolite catalyst in an olefin synthesis reactor to be converted into a hydrocarbon product containing $C_2$-$C_5$ olefins.

<Feedstock Gas>

In the first method for producing lower olefins of the present invention, any feedstock gas may be used as long as it contains dimethyl ether and it may be a gas consisting wholly of dimethyl ether or a mixed gas consisting of dimethyl ether and other components. The feedstock gas used in the present invention is preferably a gas containing, as a reaction component, only dimethyl ether, or dimethyl ether and methanol. The feedstock gas may contain, as a component other than the reaction component, inert gas for the reaction, such as steam (vapor), nitrogen and the like. As the feedstock gas used in the present invention such as this, there may be mentioned a gas consisting only of dimethyl ether, a gas consisting of dimethyl ether and methanol, a mixed gas of one of these and inert gas for the reaction, and the like. As such a feedstock gas, for example, there may be suitably used a mixed gas (containing dimethyl ether, unreacted methanol and steam) which is a crude product obtained from the reaction in which dimethyl ether is produced from methanol. Dimethyl ether may be produced from methanol, for example, by the dehydration reaction of methanol using a catalyst such as alumina and the like.

In the present invention, it is preferable that the molar ratio of dimethyl ether to methanol (dimethyl ether:methanol) in the reaction components of the feedstock gas is in the range of 6:0 to 6:5. If the ratio of methanol contained is larger than the above range, the temperature rise of the catalyst bed is excessive and the temperature rise may not be sufficiently suppressed.

Although the ratio of the reaction components in a feedstock gas depends on the amount of an additive gas used and is not specifically limited, it is 50% by volume or more and preferably about 75 to about 100% by volume.

<Zeolite Catalyst>

In the first method for producing lower olefins of the present invention, a zeolite catalyst is used for the synthesis reaction of the olefin. That is, in the method for producing lower olefins of the present invention, an olefin synthesis reactor provided with a zeolite catalyst is used. In the case of using multiple olefin synthesis reactors, the zeolite catalyst provided for each olefin synthesis reactor may be of the same kind or different for each reactor, and is preferably of the same kind of catalyst.

As the zeolite catalyst, there may be used any zeolite catalyst which can convert dimethyl ether into lower olefins and there may be preferably used a zeolite catalyst having an MFI structure such as ZSM-5 and the like. Further, the zeolite may contain an oxide other than silica and alumina in the crystal structure. In addition, the zeolite catalyst used in the present invention has an atomic ratio of silicon to aluminum (Si/Al) in the catalyst in the range of 50 to 300 and preferably 50 to 200 by molar ratio.

Further, the zeolite catalyst used in the present invention preferably contains an alkaline earth metal M such as calcium, strontium and the like, and it has an atomic ratio of the alkaline earth metal M to aluminum (M/Al) in the catalyst of 0.5 or more, preferably 0.75 to 15 and more preferably 2 to 8. The zeolite catalyst containing such an alkaline earth metal M may be prepared by a known method, for example, it is appropriately prepared by the method described in Japanese Laid-Open Patent Publication No. 2005-138000.

Here, the atomic ratio, Si/Al and M/Al may be determined by a conventional analytical method, for example, such as atomic absorption spectrometry, inductively coupled plasma emission spectrometry and the like, or either by the stoichiometric ratio of the silicon-containing compound to the aluminum-containing compound used for the synthesis of the zeolite or the stoichiometric ratio of a compound containing an alkaline earth metal M to the aluminum-containing compound.

<First Production Method>

In the first method for producing lower olefins of the present invention, a reaction for producing a hydrocarbon product containing $C_2$-$C_5$ olefins from a feedstock gas is carried out by introducing a feedstock gas containing dimethyl ether or dimethyl ether and methanol together with an additive gas into an olefin synthesis reactor filled with a zeolite catalyst and then bringing the feedstock gas into contact with the zeolite catalyst. The olefin synthesis reactor used here may be any of a fixed-bed, a moving-bed and a fluidized-bed. In the present invention, the additive gas refers to a gas fed through a line which is different from that for the feedstock gas.

In the first method for producing lower olefins of the present invention, the ratio of steam is in the range of 5 to 30% by volume and preferably 8 to 25% by volume in the feed gas composed of the feedstock gas and the additive gas, that is, in the whole gaseous component introduced into the olefin synthesis reactor. Although the amount of steam in such a feed gas is substantially small compared to that of a conventional method using a dilution gas containing steam, satisfactory suppression of the precipitation of carbon on the surface of the zeolite catalyst may be achieved and the irreversible deactivation of the zeolite catalyst caused by steam may be effectively suppressed.

The olefin synthesis reactors used in the first production method of the present invention may be single or multiple. If multiple olefin synthesis reactors are used, the olefin synthesis reactors may be connected in series, in parallel or in a combination thereof and, for example, the feedstock gas may be subjected to multistage treatment by using the reactors connected in series.

In the present invention, a feed gas refers to the total of a feedstock gas and an additive gas. In the present invention, the feedstock gas and the additive gas may be mixed in advance to be introduced into the olefin synthesis reactor as a feed gas or may be introduced separately. In the present invention, when there are multiple gas introducing inlets to the olefin synthesis reactor, or when multiple olefin synthesis reactors are used in combination, the total of gaseous components introduced into the whole reaction system is the feed gas.

In the case of using multiple olefin synthesis reactors, as long as the ratio of steam in the feed gas introduced into the whole reaction system is in the range of 5 to 30% by volume, the ratio of steam in the feed gas introduced into each olefin synthesis reactor is not specifically limited, but the ratio of steam in the feed gas introduced into each reactor is preferably in the range of 5 to 30% by volume.

In the present invention, when lower olefins are produced using multiple olefin synthesis reactors connected in series, it is preferable that a feedstock gas containing dimethyl ether be divided and fed into each reactor and simultaneously an additive gas be introduced into the most upstream reactor, followed by bringing the feedstock gas into contact with a zeolite catalyst in each reactor to be converted into a hydrocarbon product containing $C_2$-$C_5$ olefins. Here, the hydrocarbon product obtained from the upstream reactor is sequentially introduced into the downstream reactor, and propylene and ethylene when needed are separated and recovered from the hydrocarbon product obtained from the most downstream reactor and then at least a part of the remainder after separating propylene and ethylene when needed may be used as at least a part of the additive gas. Here, relative to the total amount (feed gas) of all the feedstock gases and the additive gas introduced into each reactor, the ratio of steam contained in the total amount is preferably in the range of 5 to 30% by volume.

Figure 2:
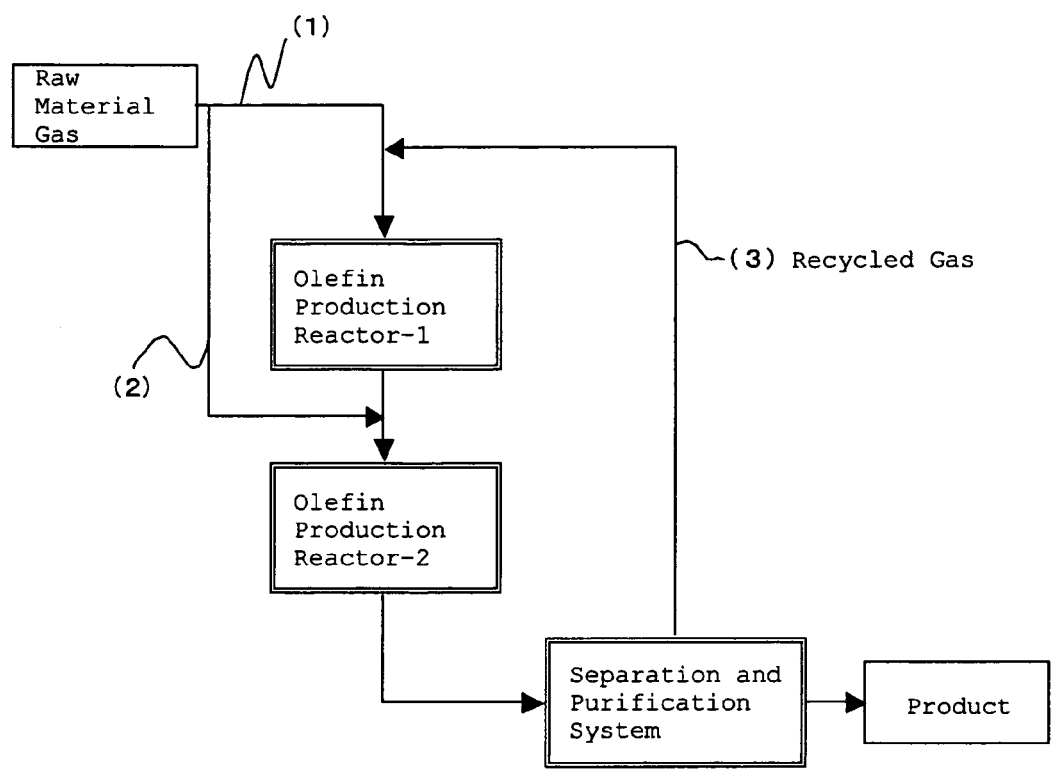
FIG. 2 is a schematic diagram showing an embodiment of the first invention in the case of using two olefin synthesis reactors connected in series.

Here, as shown in the flow diagram of FIG. 2, in the case of producing lower olefins using two olefin synthesis reactors connected in series and in the reaction system in which a feedstock gas (1) such as dimethyl ether and the like and an additive gas (3) which is a recycled gas are fed into the most upstream olefin synthesis reactor 1, the total amount of the hydrocarbon product containing $C_2$-$C_5$ olefins obtained in the reactor 1 is introduced into the downstream reactor 2 and a feedstock gas (2) is further additionally fed into the downstream reactor (2), the total of (1), (2) and (3) corresponds to the feed gas in the present invention. Here, since the hydrocarbon product obtained in the reactor (1) contains steam that is produced as a by-product in the dehydration reaction in which $C_2$-$C_5$ olefins are obtained from dimethyl ether (or dimethyl ether and methanol), the ratio of steam in the total amount may be easily controlled to 5 to 30% by volume also for the feed gas regarding the individual reactor 1 and reactor 2, without newly adding steam to be introduced into the reactor 2.

Figure 3:
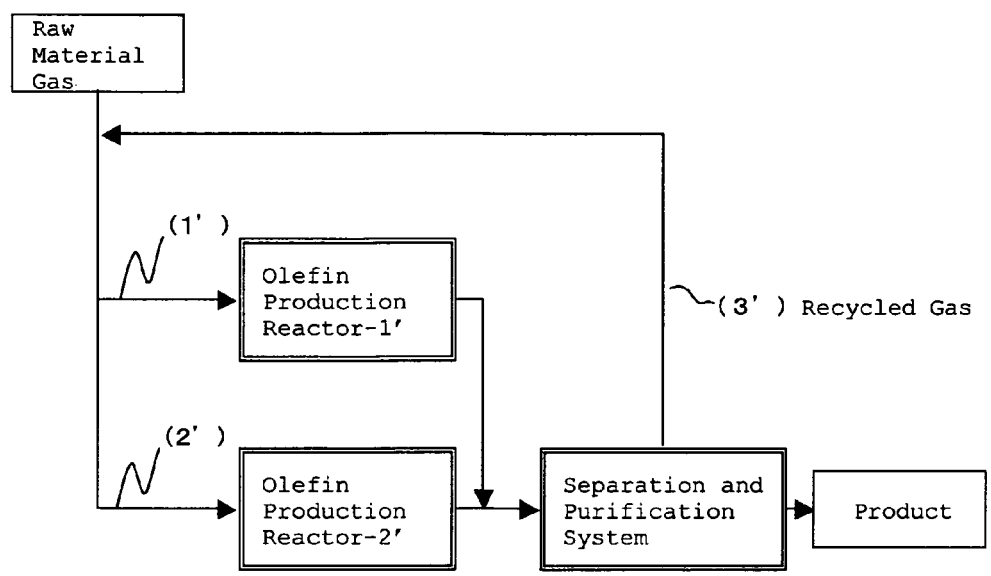
FIG. 3 is a schematic diagram showing an embodiment of the first invention in the case of using two olefin synthesis reactors connected in parallel.

In addition, as shown in the flow diagram of FIG. 3, in the case of producing lower olefins using two olefin synthesis reactors connected in parallel, a feedstock gas (1') or (2') such as dimethyl ether and the like and an additive gas (3') which is a recycled gas are fed into olefin synthesis reactors 1' and 2', respectively, and the hydrocarbon product containing the $C_2$-$C_5$ olefin obtained in each reactor is introduced into the downstream separation and purification system to separate propylene (or ethylene and propylene), followed by using at least a part of the remainder after separation as an additive gas (3'). Here, a feed gas defined in the present invention is the total of the feedstock gases (1'), (2') and the additive gas (3'). In the flow diagram of FIG. 3, although separation and purification of the hydrocarbon product are simultaneously carried out, in the system of using multiple olefin synthesis reactors in parallel, the hydrocarbon product obtained from each olefin synthesis reactor may be separated and purified separately.

In the present invention, in the case of using multiple olefin synthesis reactors, there may be selected the reaction conditions in each reactor, the type and amount of a catalyst, the feed amount of a feed gas, the ratio of a feedstock gas to an additive gas in the feed gas, and the like, depending on the production amount of a desired product and the like, which may be different for each olefin synthesis reactor.

In the present invention, in the olefin synthesis reactor, a feedstock gas, is brought into contact with a zeolite catalyst to obtain a hydrocarbon product containing $C_2$-$C_5$ olefins from the olefin synthesis reactor.

There may be set as appropriate the conditions such as the feed rate of a feedstock gas and an additive gas into an olefin synthesis reactor, the gas pressure, the reaction temperature and the like, taking into consideration the yield of a desired lower olefin, the catalyst life and the like. In the present invention, 55% or more (in terms of carbon) of the feedstock gas introduced may be finally converted into propylene by suitably setting the type of a catalyst and the reaction conditions. From the viewpoint of the yield of lower olefins, the life of the zeolite catalyst and the like, the flow rate of a feedstock gas is set so that the WHSV (weight-hourly space velocity) is preferably 0.025 to 5 $h^{-1}$ and more preferably 0.1 to 3 $h^{-1}$.

The reaction pressure is preferably 0.005 to 1.5 MPa and more preferably 0.02 to 1.0 MPa as the partial pressure of a feedstock gas. In addition, the reaction temperature is preferably 350 to 750° C. and more preferably 400 to 650° C.

From the resulting hydrocarbon product, ethylene and propylene or only propylene are separated and recovered as a product. In the present invention, components other than ethylene and/or propylene may be separated and recovered from the hydrocarbon product as desired. The separation and recovery of ethylene and/or propylene from the hydrocarbon product may be carried out by a known method, for example, by fractional distillation.

The remainder after separating ethylene and/or propylene from the hydrocarbon product contains light paraffins such as methane and the like, $C_4$ and $C_5$ olefins and aromatic compounds. In the present invention, at least a part of the remainder is used as at least a part of the above-mentioned additive gas. In other words, in the present invention, the remainder after separating propylene and ethylene when needed from the hydrocarbon product may be entirely recycled to be introduced into the olefin synthesis reactor as an additive gas, or a part of the remainder may be separated and used. In the case of separating and recovering only propylene from the hydrocarbon product, ethylene in the remainder may be recycled as a whole to be used as an additive gas or may be converted into a hydrocarbon having four or more carbon atoms by dimerization and the like to be used as a part of an additive gas.

Further, in the present invention, the total amount of the additive gas may be derived from the remainder after separating propylene and ethylene when needed from the hydrocarbon product and may contain the remainder and other gases. In the present invention, there is preferably used an additive gas containing a recycled gas, that is, components derived from the remainder after separating propylene and ethylene when needed from the hydrocarbon product at a ratio of 50% by volume or more and preferably approximately 60 to 90% by volume of the additive gas. In the present invention, since there is used an additive gas in which the amount of steam and the amount of $C_4$ and/or $C_5$ olefins are controlled closely, the amount of water to be recycled may be reduced by minimizing the dilution of the feedstock gas with steam, and the process is economical because the thermal efficiency is increased.

In the present invention, the additive gas may be used depending on the component and the amount of the feedstock gas so that the ratio of steam in the total amount of the feed gas is 5 to 30% by volume. The additive gas is preferably used in an amount so that the ratio of the additive gas excluding steam to the feedstock gas is in the range of 0.2 to 5.0 by the ratio of the number of moles of the additive gas excluding steam to the number of moles of the feedstock gas on a carbon basis. In addition, the total amount of $C_4$ and $C_5$ olefins in the additive gas to the total amount of methanol and dimethyl ether in the feedstock gas (the total amount of $C_4$ and $C_5$ olefins in the additive gas/the total amount of methanol and dimethyl ether in the feedstock gas) is preferably in the range of 0.3 to 5.0 by molar ratio on a carbon basis. If a feed gas in which the feedstock gas and the additive gas satisfy the above relationship is used, precipitation of carbonaceous deposits on the surface of zeolite catalyst may be effectively suppressed without adding a large amount of steam, thereby enabling the extension of the usage time to the reversible deactivation of a zeolite catalyst and effective suppression of the irreversible deactivation caused by the extraction of aluminum from the framework structure of the zeolite catalyst.

In such a method for producing lower olefins of the present invention, when a zeolite catalyst temporarily deactivated is subjected to a regeneration treatment, the zeolite catalyst shows a catalytic activity equivalent to that at the initial use and the formation of carbonaceous deposits on the surface of the zeolite catalyst is effectively suppressed, thereby allowing continuous production of the lower olefin for a long period of time. The propylene selectivity refers to a ratio of the amount of produced propylene in the total amount of the hydrocarbon product (on a carbon basis) obtained in the whole reaction system per unit time. That is, the propylene selectivity in the hydrocarbon product is represented by the following equation.

Propylene selectivity (%)=(The rate of propylene production on a carbon basis in the total amount of the hydrocarbon product)×100/(The rate of production of the total hydrocarbon product on a carbon basis) [Equation 1]

However, in the present invention, since the hydrocarbon product refers to the total amount of the distillate obtained from the exit of the olefin synthesis reactor, "the total hydrocarbon product" contains both a component obtained by the reaction and an unreacted component or a component inactive in the reaction. For this reason, the propylene selectivity obtained from the above equation is not the propylene selectivity in the lower olefins obtained strictly by the reaction, and the propylene selectivity in the lower olefins produced by the reaction has a higher value.

Second Production Method of Lower Olefins

In the second method for producing lower olefins of the present invention, a feedstock gas containing dimethyl ether is brought into contact with a zeolite catalyst in a reactor using multiple olefin synthesis reactors to convert into a hydrocarbon product containing lower olefins of about $C_2$-$C_5$. As the feedstock gas and the zeolite catalyst, there may be suitably used those similar to the feedstock gas and the zeolite catalyst used in the first method for producing the lower olefin mentioned above. The multiple olefin synthesis reactors used in the second production method of the present invention are each provided with a zeolite catalyst. The zeolite catalyst provided for each olefin synthesis reactor may all be the same type or may be different for each reactor, but is preferably the same type.

<Additive Gas>

In the second method for producing lower olefins of the present invention, an additive gas is a gas fed through a line different from that for the feedstock gas.

The additive gas need not be used if the above-mentioned feedstock gas contains a relatively large amount of an inactive component (component other than the reaction components), but the additive gas is preferably introduced into the reaction system together with the feedstock gas. The additive gas may be directly introduced into the reaction system or may be introduced by mixing with the feedstock gas before introducing into the reactor.

As the additive gas, specifically, there may be suitably used a gas composed mainly of inert gas to the reaction of the lower olefin production such as nitrogen and the like.

In addition, as the additive gas, there may be suitably used a gas containing hydrocarbons such as $C_4$ and $C_5$ olefins and the like.

As the gas containing hydrocarbons such as $C_4$ and $C_5$ olefins and the like, there may be suitably used what is called a recycled gas, which is at least a part of hydrocarbons that are the remainder after separating lower olefins containing propylene from the product obtained from the most downstream olefin synthesis reactor of the present invention.

In addition, as the gas containing hydrocarbons such as $C_4$ and $C_5$ olefins and the like, there may be preferably used a gas introduced from the outside of the system for producing lower olefins of the present invention, for example, there may be suitably used at least a part of gas of hydrocarbons, which are the remainder after separating lower olefins containing propylene from the product obtained in an olefin producing unit for producing olefins by thermal cracking and/or catalytic cracking of hydrocarbons. In other words, as the additive gas or a part of the additive gas, there may be used a part or all of the remainder after separating lower olefins product from the product obtained from an olefin producing unit for producing olefins by thermal cracking and/or catalytic cracking of hydrocarbons, for example, a naphtha cracker, a fluid catalytic cracking (FCC) unit and the like.

All of the gases containing hydrocarbons such as $C_4$ and $C_5$ olefins and the like, which are a recycled gas or a gas introduced from the outside of the system, are a gas containing the remainder after separating lower olefins product from the product obtained by the reaction producing lower olefins and the like, and typically are a mixed gas of $C_4$ and/or $C_5$ olefins, light paraffins such as methane and the like and aromatics and the like or composed of a part thereof. Such gases preferably are a gas composed mainly of at least a part of hydrocarbons that are the remainder after separating propylene which is the desired lower olefin and ethylene when needed from the product obtained by the reaction and specifically $C_4$ and/or $C_5$ olefins fraction.

The additive gas used in the second method for producing lower olefins of the present invention may consist only of a gas which is inactive to the reaction and introduced from outside the system, may consist only of a gas containing $C_4$ and/or $C_5$ olefins which are introduced from a unit outside the system such as an olefin producing unit for producing olefins by thermal cracking and/or catalytic cracking of hydrocarbons, may consist only of a recycled gas introduced from a reactor inside the system such as an olefin synthesis reactor at the most downstream and may be a mixed gas of those gases introduced from inside and outside of the system. The additive gas used in the second method for producing lower olefins of the present invention preferably contains a component derived from a gas containing $C_4$ and/or $C_5$ olefins introduced from a unit outside the system or a recycled gas at a ratio of 50% by volume or more and preferably about 60 to about 100% by volume of the additive gas.

If $C_4$ and/or $C_5$ olefins are contained in the additive gas, the yield of propylene may be further increased by the reaction of the $C_4$ and $C_5$ olefins. For this reason, in the present invention, the additive gas preferably contains $C_4$ and/or $C_5$ olefins. If the additive gas contains $C_4$ and/or $C_5$ olefins, the olefins are preferably derived from a recycled gas from the olefin synthesis reactor at the most downstream or a gas obtained from an olefin producing unit for producing olefins by thermal cracking and/or catalytic cracking of hydrocarbons, but may be derived from a gas obtained from another unit outside the system.

<Feed Gas>

In the second method for producing lower olefins of the present invention, multiple olefin synthesis reactors connected in series are used, and in the present invention, a feed gas refers to the total of a feedstock gas introduced into all the reactors and an additive gas.

In the second method for producing lower olefins of the present invention, steam is preferably contained in the feed gas and the ratio of steam in the feed gas is 5 to 30% by volume and is preferably in the range of 8 to 25% by volume. If steam is present in the reaction system, the formation of carbonaceous deposits is suppressed and as a result, it is expected that the catalyst life to the reversible deactivation is extended. Here the term "reversible deactivation" represents deactivation of a catalyst caused by accumulation of carbonaceous deposits that are produced as by-products during the reaction and the catalyst may be regenerated by burning in air and the like. On the other hand, the presence of a large amount of steam in the reaction system is not preferable because the irreversible deactivation is caused by extraction of aluminum in a zeolite catalyst. The irreversible deactivation represents deactivation which prevents regeneration of the catalyst by any treatment. For this reason, the amount of steam in the feed gas is preferably set to the above range by controlling the composition and the amount used of the feedstock gas and the additive gas. Such amount of steam in the feed gas is extremely small as compared to that of a conventional method in which an additive gas containing steam is used, but may sufficiently exhibit an effect of suppressing the formation of carbonaceous deposits on the surface of the zeolite catalyst and may effectively suppress the irreversible deactivation of the zeolite catalyst caused by steam.

In the second production method of the present invention, the ratio of a component other than the reaction components excluding steam to the reaction components in the feed gas, which is not particularly limited, is preferably in the range of 0.2 to 5.0 by the ratio of the number of moles of the component other than the reaction components excluding steam to the number of moles of the reaction components on a carbon basis.

In addition, in the second production method of the present invention, the feed gas preferably contains also $C_4$ and/or $C_5$ olefins. The $C_4$ and/or $C_5$ olefins in the feed gas are typically derived from the additive gas and may be contained in advance in the feedstock gas as a component other than the reaction components. The amount of the $C_4$ and/or $C_5$ olefins in the feed gas is not particularly limited, but it is preferable that the ratio thereof to the amount of the reaction components be approximately 0.3 to 5.0 by molar ratio on a carbon basis, because the ratio is particularly effective for increasing the propylene yield. If $C_4$ and/or $C_5$ olefins are contained in the feed gas, these hydrocarbons become a raw material for propylene, thereby not only improving the propylene yield in the process but also reducing the amount of generated heat by a dilution effect and the like and further bringing about the effect of extending the catalyst life. In other words, in the second production method of the present invention, if the feed gas contains $C_4$ and/or $C_5$ olefins, there may be further expected the following advantages: the increase in the propylene yield, stabilization effect of the catalyst bed temperature and extension effect of the catalyst life.

<Second Production Method>

In the second method for producing lower olefins of the present invention, multiple olefin synthesis reactors connected in series are used. Each olefin synthesis reactor connected may have an equal processing capacity or may have a different processing capacity. That is, each olefin synthesis reactor connected may be provided with the same amount of a zeolite catalyst or may be provided with a different amount of the zeolite catalyst.

Figure 4:
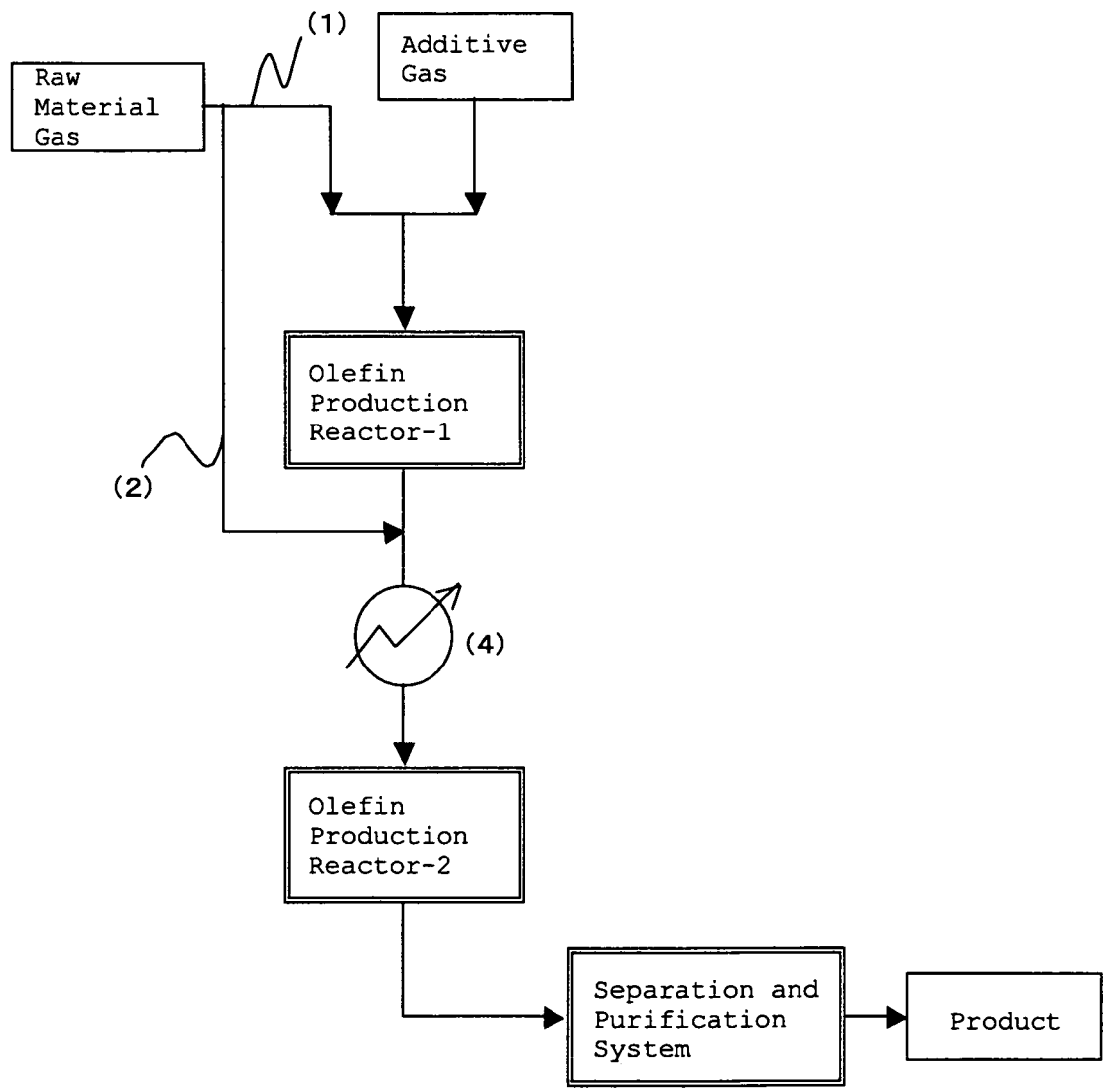
FIG. 4 shows an example of a diagram of a suitable embodiment carrying out the second invention.
Figure 5:
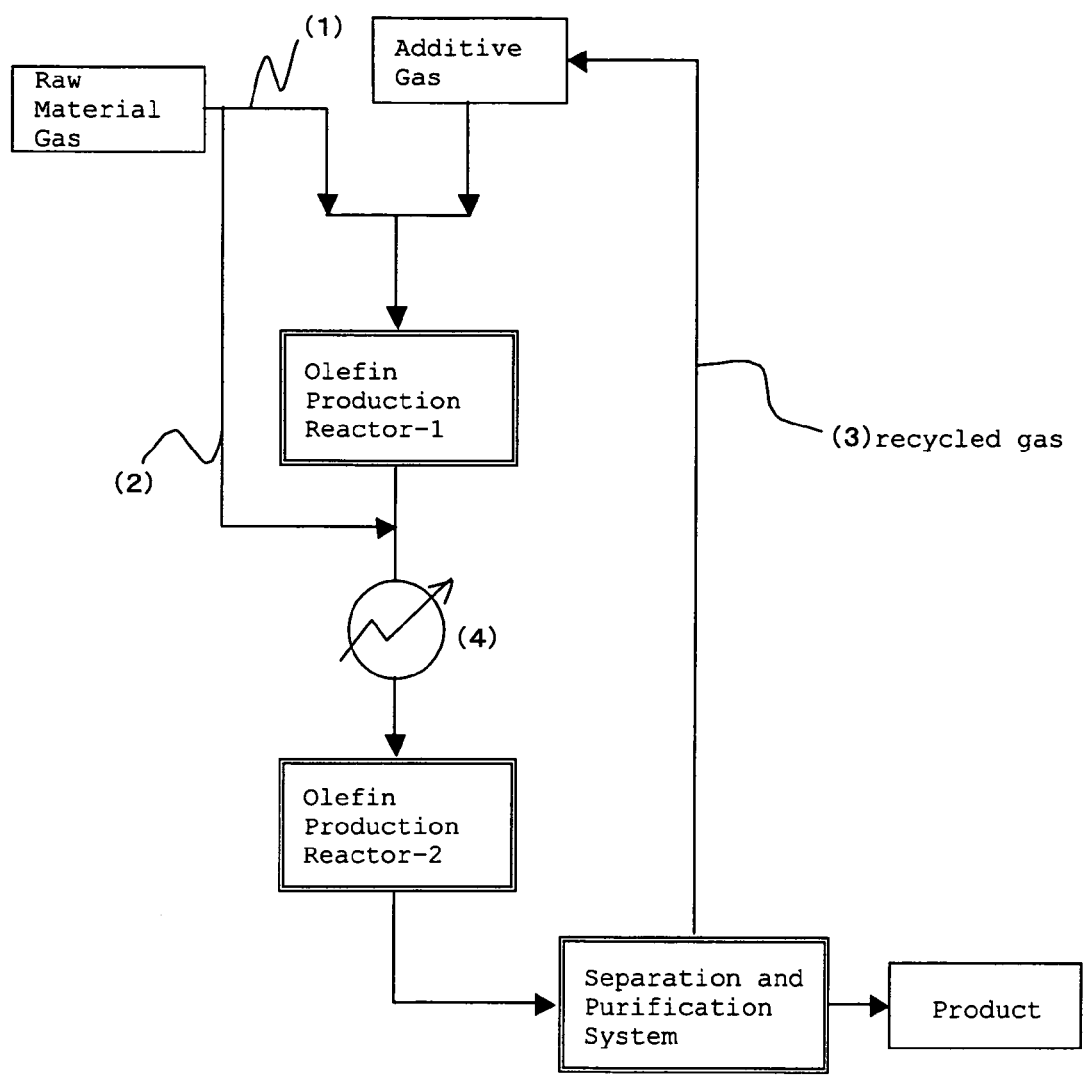
FIG. 5 is an example of a diagram of a suitable embodiment carrying out the second invention and shows an embodiment using the recycled gas as an additive gas.
Figure 6:
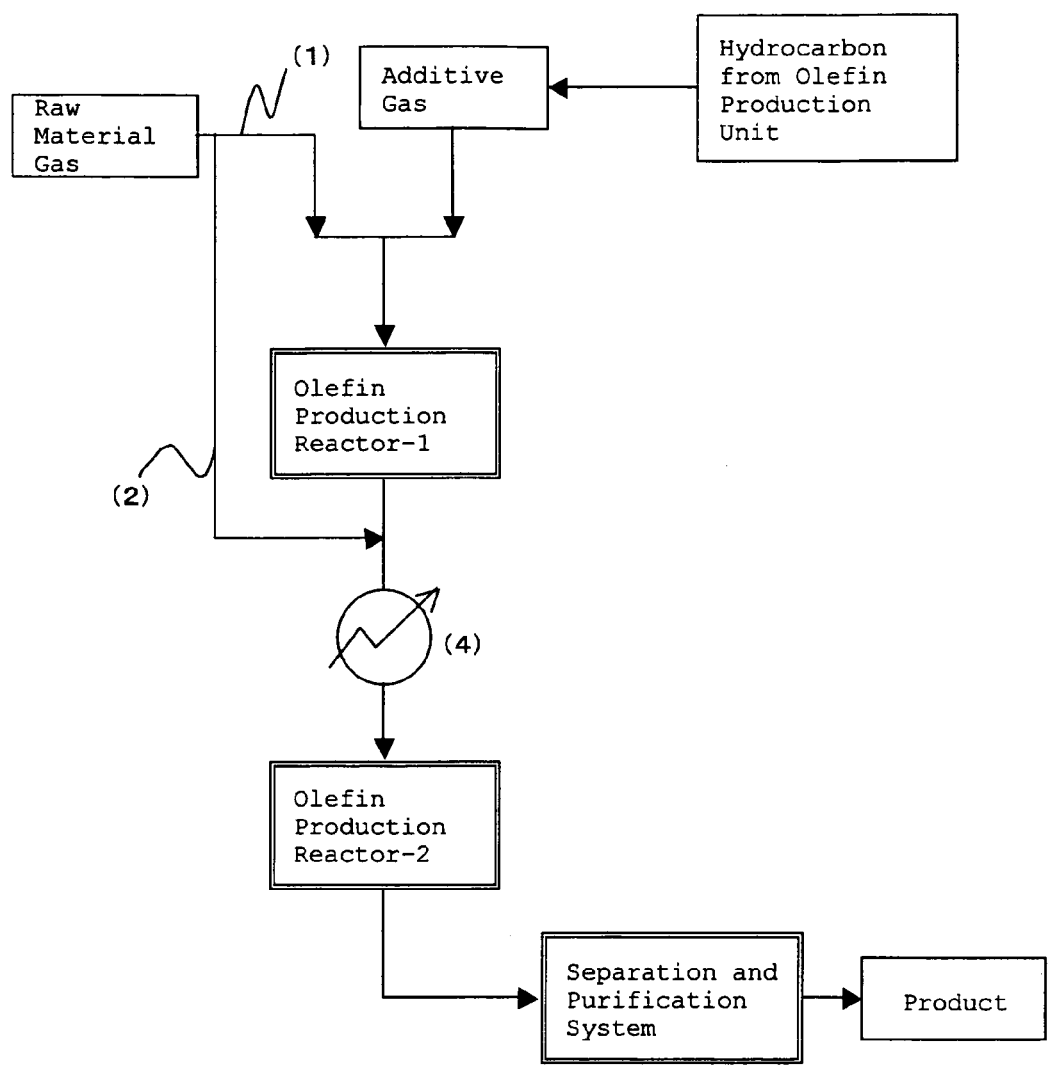
FIG. 6 is an example of a diagram of a suitable embodiment carrying out the second invention and shows an embodiment using the hydrocarbon derived from a product obtained from an olefin producing unit outside the system as an additive gas.

In the present invention, the connection in series, for example as shown in FIGS. 4 to 6 illustrating the schematic diagram of preferred embodiments of the second production method of the present invention, is a state in which the total amount of the components discharged from an upstream reactor is fed into a downstream reactor connected adjacently. The components discharged from the upstream reactor contain a reaction product generated by the reaction of reaction components in a feedstock gas and an additive gas in the upstream reactor, non-reactive components in the raw material and additive gases and unreacted components depending on the conditions.

Between each olefin synthesis reactor connected, a cooling system such as a heat exchanger and the like may be provided, with which the product from the upstream olefin synthesis reactor may be cooled and fed into the downstream olefin synthesis reactor.

In the second production method of the present invention, a raw material is divided and fed into two or more olefin synthesis reactors. In other words, if two olefin synthesis reactors are connected in series, the feedstock gas is fed into each of the two reactors, and if three or more olefin synthesis reactors are connected in series, the feedstock gas is fed into two or more of them. In the case of using three or more olefin synthesis reactors connected in series, there may be a reactor into which the divided feedstock gas is not newly fed, but the feedstock gas is required to be fed at least into the most upstream reactor, and preferably, the divided feedstock gas is fed into all the reactors.

The feedstock gas may be divided equally or at a different ratio to be fed into each of the olefin synthesis reactors, but if each olefin synthesis reactor connected is provided with the same type and amount of a catalyst, the feedstock gas is preferably divided equally and fed. If the type or amount or both of them of the catalyst filled in each olefin synthesis reactor may be different and there may be a difference in the processing capacity, the feedstock gas is preferably divided and fed into each olefin synthesis reactor at a ratio according to the processing capacity.

In the second production method of the present invention, it is vital that a space velocity, which is represented by the feed rate (g/h) of all the feedstock gases (the total of the feedstock gases fed into all the olefin synthesis reactors) per unit time to the total amount (g) of the catalyst in all the olefin synthesis reactors, is in the range of 0.5 to 50 $h^{-1}$, preferably 1.0 to 10 $h^{-1}$ and more preferably 1.0 to 5.0 $h^{-1}$ by WHSV on the basis of dimethyl ether.

Here, the space velocity (WHSV) is, in other words, the feed weight (g-DME) of the reaction components (the total of dimethyl ether and methanol) equivalent to dimethyl ether per unit time (h) and unit catalyst weight (g-cat) and is a value (unit is $h^{-1}$) determined by the following equation:

$$(g\text{-DME})/(g\text{-cat})/(h)$$

If the space velocity (WHSV) is less than 1.0 $h^{-1}$, it is not suitable for the practical operations in the industrial production because the propylene selectivity in the lower olefins produced is low and the effect of the present invention due to the divided feeding of a raw material may not be obtained.

If the space velocity (WHSV) is approximately in the range of 1.0 to 4.0 $h^{-1}$, the propylene yield is improved with the increase in WHSV, and if the space velocity is larger than approximately 4.0 $h^{-1}$, there may not be expected a further increase in the propylene yield with the increase in WHSV but a high propylene yield is maintained and the space time yield is increased with the increase in WHSV. However, WHSV larger than 50 $h^{-1}$ is not practical because the time to the reversible deactivation caused by the formation of carbonaceous material is shortened.

In the second method of the present invention, when an additive gas is introduced into the reaction system, the additive gas may be introduced into each olefin synthesis reactor, but is preferably introduced only into the most upstream reactor among the multiple olefin synthesis reactors connected in series. In the present invention, since the olefin synthesis reactors are connected in series and the total amount of the additive gas fed into an upstream reactor and the product is continuously introduced into a downstream reactor, the partial pressure of a raw material in each rector may be most efficiently reduced by introducing the additive gas only into the most upstream reactor, and as a result the improvement of the propylene yield is expected, and the control of facilities and operation may be simplified by feeding the additive gas only into one reactor.

In each olefin synthesis reactor, the pressure in the reaction system is preferably 0.05 to 1.5 MPa and more preferably 0.02 to 1.0 MPa as a partial pressure of a feedstock gas. In addition, the reaction temperature is preferably 350 to 750° C. and more preferably 350 to 650° C.

In the second production method of the present invention, all the products containing lower olefins after the reaction may be obtained from the most downstream olefin synthesis reactor. Only both ethylene and propylene or propylene are separated and recovered as lower olefins product from a mixture containing reaction products obtained from the most downstream olefin synthesis reactor. In the present invention, components other than ethylene and/or propylene may be separated and recovered from a mixture containing the product, if desired. The separation and recovery of ethylene and/or propylene from the mixture containing the product may be carried out by a known method, for example, by fractional distillation using a separation and purification system such as a splitter and the like.

The remainder after separating lower olefin products such as propylene and the like from a mixture containing the product contains a light paraffin such as methane and the like, $C_4$ and $C_5$ olefins and aromatic compounds. In the present invention, at least a part of the remainder is used as what is called a recycled gas, which is at least a part of the above-mentioned additive gas. If only propylene is separated and recovered as lower olefins product, ethylene in the remainder may be used as it is as a recycled gas for a component of an additive gas or may be converted into a hydrocarbon having four or more carbon atoms by dimerization and the like to be used as a component of an additive gas.

In the second production method of the present invention, in practical industrial operations, the reaction components introduced as a feedstock gas, that is, dimethyl ether and methanol when needed, are preferably not present in the product, and it is desired that the conversion of the reaction components be 95% or more, preferably 99% or more and more preferably 99.9% or more. Here, the conversion is determined by the following equation, and in Examples 3 to 9 and Comparative Examples 9 to 12 to be described later, the conversion was determined by the following equation.

Conversion (%)={(Feed rate of reaction components [mol-C/hr])−(Exit rate of reaction components [mol-C/hr])}×100/(Feed rate of reaction components [mol-C/hr])     [Equation 2]

In the above equation, the reaction components refer to the total of dimethyl ether and methanol, and the feed rate and exit rate refers to a rate on a carbon basis.

In the second production method of the present invention, since it is desired that lower olefins be produced at such a high conversion of reaction components, the time when a predetermined conversion may not be accomplished may be treated as the end of a catalyst life.

The second production method of the present invention is suitably carried out, for example, by the equipment configuration shown in FIGS. 4 to 6. In these equipment configurations, a raw material is divided by lines (1) and (2) and introduced into each olefin synthesis reactor.

In the second production method of the present Invention, also preferable is an embodiment in which an additive gas contains what is called a recycled gas, which is a remainder after separating at least a part of the remainder after separating propylene and ethylene when needed from a hydrocarbon product which is produced by an olefin synthesis reactor and contains lower olefins, and the ratio of steam in a feed gas is in the range of 5 to 30% by volume. The production method of this embodiment may be suitably carried out by a flow shown in FIG. 5. Also in such a production method, as a suitable embodiment of a catalyst to be used, a feedstock gas, conditions of feeding rate of the feedstock gas and the like, there may be mentioned the similar conditions to the suitable production conditions described in the first and second production methods.

EXAMPLES

Hereinafter, the present invention will be more specifically explained based on examples, but the present invention is not limited thereto.

In Examples 1 and 2 and Comparative Examples 1 to 8, the catalyst life is measured as the time until the conversion of a feedstock gas, dimethyl ether, becomes zero from the start of the reaction and is represented as a value relative to the catalyst life that is set equal to 1.00, measured with a fresh zeolite catalyst (at the time of initial use) by using a mixed gas containing dimethyl ether and nitrogen gas at a ratio of 1:1 as a feed gas (Comparative Example 1).

Example 1

Preparation of Zeolite Catalyst A

An aqueous solution was prepared by dissolving a zeolite raw material solution consisting of 9.50 g of Al $(NO_3)_3.9H_2O$ and 10.92 g of Ca $(CH_3COO)_2.H_2O$ in 750 g of water. To the aqueous solution were added a solution in which 500 g of Cataloid Si-30 Water Glass (manufactured by Catalysts & Chemicals Ind. Co., Ltd.) is dissolved in 333 g of water, 177.5 g of 6% by mass of an aqueous NaOH solution, 317.6 g of 21.3% by mass of an aqueous tetrapropylammonium bromide solution and 15.0 g (corresponding to 10% by mass of the amount of a zeolite catalyst synthesized without adding a seed crystal) of an ammonium-type MFI structure zeolite (manufactured by Zeolyst International, Si/Al atomic ratio is 70) having an average particle size of 0.5 μm as a zeolite seed crystal under stirring to obtain an aqueous gel mixture.

Then, the aqueous gel mixture was placed in an autoclave of 3 L and the hydrothermal synthesis was carried out by stirring under the self pressure at 160° C. for 18 hours.

A white solid product obtained by the hydrothermal synthesis was filtered and washed with water, followed by drying at 120° C. for 5 hours and calcining in air at 520° C. for 10 hours.

The calcined product was soaked in 0.6 N hydrochloric acid, followed by stirring at room temperature for 24 hours to convert the type of the zeolite to a proton-type.

Thereafter, the product was filtered and washed with water and then dried at 120° C. for 5 hours, followed by calcining in air at 520° C. for 10 hours to obtain a proton-type zeolite catalyst A having the MFI structure and containing an alkaline earth metal.

The resulting zeolite catalyst A had a Si/Al atomic ratio of 100, a Ca/Al atomic ratio of 3.7, a specific surface area of 320 $m^2/g$ and an average particle size of 1.5 μm.

<Production of Lower Olefins>

The reaction for olefin production was continuously carried out by introducing a feed gas consisting of the components shown in Table 1 which combined a feedstock gas, dimethyl ether (DME) and an additive gas consisting of nitrogen, steam and isobutene into a fixed-bed flow reactor filled with the zeolite catalyst A prepared above. The reaction conditions were set at atmospheric pressure and a reaction temperature of 530° C., and the weight-hourly space velocity (WHSV), which is the ratio of the amount of the feedstock gas, dimethyl ether, fed per unit time to a unit quantity of the catalyst, was set to 9.5 g-DME/(1 g-catalyst·hour). Here, the additive gas is a simulated recycled gas containing isobutene corresponding to the olefin component, nitrogen gas corresponding to the component inactive for the reaction of producing lower olefins and steam.

The component analysis of the reactor exit gas was carried out by gas chromatography. In addition, the catalyst life to the reversible deactivation was represented by a relative life by setting the catalyst life obtained in Comparative Example 1 described later equal to 1, where a freshly prepared catalyst was used and a feed gas not containing isobutene and steam was introduced.

The results are shown in Table 1.

Example 2

The catalyst used in Example 1 the life of which expired was regenerated by calcining at 550° C. for 10 hours in an air flow, and the lower olefin production was carried out in a similar manner as in Example 1 except that the regenerated catalyst obtained was used. The results are shown in Table 1.

Comparative Example 1

In Example 1, the lower olefin production and component analysis of the reactor exit gas were carried out in a similar manner as in Example 1 by using as a feed gas a mixed gas of 50% by volume of a feedstock gas, dimethyl ether, and 50% by volume of nitrogen as an additive gas. The results are shown in Table 1.

Comparative Example 2

The catalyst used in Comparative Example 1 the life of which expired was regenerated by calcining at 550° C. for 10 hours in an air flow, and the lower olefin production was carried out in a similar manner as in Comparative Example 1 except that the regenerated catalyst obtained was used. The results are shown in Table 1.

Comparative Example 3

In Example 1, the lower olefin production and component analysis of the reactor exit gas were carried out in a similar manner as in Example 1 by using as a feed gas a mixed gas of 42% by volume of a feedstock gas, dimethyl ether, 34% by volume of nitrogen and 24% by volume of isobutene as an additive gas. The results are shown in Table 1.

Comparative Example 4

The catalyst used in Comparative Example 3 the life of which expired was regenerated by calcining at 550° C. for 10 hours in an air flow, and the lower olefin production was carried out in a similar manner as in Comparative Example 3 except that the regenerated catalyst obtained was used. The results are shown in Table 1.

Comparative Example 5

In Example 1, the lower olefin production and component analysis of the reactor exit gas were carried out in a similar manner as in Example 1 by using as a feed gas a mixed gas of 25% by volume of a feedstock gas, dimethyl ether, 50% by volume of nitrogen and 25% by volume of steam as an additive gas. The results are shown in Table 1.

Comparative Example 6

The catalyst used in Comparative Example 5 the life of which expired was regenerated by calcining at 550° C. for 10 hours in an air flow, and the lower olefin production was carried out in a similar manner as in Comparative Example 5 except that the regenerated catalyst obtained was used. The results are shown in Table 1.

Comparative Example 7

In Example 1, the lower olefin production and component analysis of the reactor exit gas were carried out in a similar manner as in Example 1 by using as a feed gas a mixed gas of 33% by volume of a feedstock gas, dimethyl ether, 32% by volume of nitrogen and 35% by volume of steam as an additive gas. The results are shown in Table 1.

Comparative Example 8

The catalyst used in Comparative Example 7 the life of which expired was regenerated by calcining at 550° C. for 10 hours in an air flow, and the lower olefin production was carried out in a similar manner as in Comparative Example 7 except that the regenerated catalyst obtained was used. The results are shown in Table 1.

TABLE 1

| | Example 1 | Example 2 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|
| Catalyst | New | Regenerated | New | Regenerated | New | Regenerated | New | Regenerated | New | Regenerated |
| Feed gas Component (% by volume) | | | | | | | | | | |
| DME | 39 | 39 | 50 | 50 | 42 | 42 | 25 | 25 | 33 | 33 |
| $N_2$ | 7 | 7 | 50 | 50 | 34 | 34 | 50 | 50 | 32 | 32 |
| $H_2O$ (Steam) | 28 | 28 | 0 | 0 | 0 | 0 | 25 | 25 | 35 | 35 |
| Isobutene | 26 | 26 | 0 | 0 | 24 | 24 | 0 | 0 | 0 | 0 |
| Steam Concentration at reactor inlet (% by volume) | 28 | 28 | 0 | 0 | 0 | 0 | 25 | 25 | 35 | 35 |

TABLE 1-continued

|  | Example 1 | Example 2 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|
| Steam Concentration at reactor exit (% by volume) | 54 | 54 | 44 | 42 | 32 | 32 | 43 | 44 | 61 | 61 |
| Propylene Selectivity (%) | 33 | 34 | 31 | 32 | 36 | 36 | 39 | 39 | 37 | 37 |
| Relative Life | 2.32 | 2.23 | 1.00 | 0.98 | 1.86 | 1.80 | 1.57 | 1.47 | 1.86 | 0.72 |

The following matters were confirmed from the results of Examples 1 and 2 and Comparative Examples 1 to 8.

In a comparison of Example 1 in which a feedstock gas was diluted only with nitrogen with Comparative Example 5 in which a feedstock gas was diluted with steam, it is found that the catalyst life (the time to the reversible deactivation caused by the formation of carbonaceous deposits) is substantially extended when a feedstock gas is diluted with steam. In addition, since the catalyst life is further extended in Comparative Example 7 in which the concentration of added steam is further increased, it is found that the catalyst life is extended in proportion to the steam concentration. On the one hand, from the results of Comparative Examples 1 and 2, Comparative Examples 5 and 6, and Comparative Examples 7 and 8, it is shown that, if the steam concentration in a feed gas is increased to 30% by volume or more, the time until the regenerated catalyst is deactivated is rapidly shortened, which indicates the occurrence of irreversible deactivation in which aluminum is irreversibly removed from the framework structure of the zeolite catalyst in the presence of a high concentration of steam, resulting in the reduction of active sites.

On the contrary, from Examples 1 and 2, the present invention in which the amount of steam and the amount a $C_4$ olefin in a feed gas is controlled in a specific range shows that the catalyst life at the time of initial use is significantly extended, and even when the regenerated catalyst is used, it is shown that the life is comparable to the catalyst life at the time of initial use and the time to the reversible deactivation may be substantially extended without practically causing the irreversible deactivation.

Even in Comparative Example 3 in which a feedstock gas was diluted with a $C_4$ olefin, isobutene, the catalyst life is extended similarly in the case of the steam addition, and even in Comparative Example 4 performed after the catalyst regeneration, the life is confirmed not to be shortened. However, in comparing the relative life of Example 1 and Comparative Example 3 and the relative life of Example 2 and Comparative Example 4, respectively, Example 1 and Example 2 have a longer relative life and the relative life of a catalyst is more effectively extended by the use of an additive gas in which an appropriate amount of steam is added to isobutene.

Further, in Examples 1 and 2, the thermal efficiency of the process may be increased by reducing the amount of water to be recycled because a large amount of water may not be used as an additive gas, and there may be accomplished deletion or substantial scale reduction of the facilities related to the recycling of water and steam generation, thereby enabling to reduce the operation cost and the construction cost.

In the following Examples 3 to 9 and Comparative Examples 9 to 12, the catalyst life was defined as the time until the conversion of the reaction components is less than 99.9%, that is, the time until 0.1% of the reaction components (the total amount of dimethyl ether and methanol) used as a raw material is found in a mixture containing lower olefins obtained from the olefin synthesis reactor at the most downstream.

Preparation Example 1

Preparation of Zeolite Catalyst B

An aqueous solution was prepared by dissolving a zeolite raw material solution consisting of 9.50 g of Al$(NO_3)_3.9H_2O$ and 10.92 g of Ca$(CH_3COO)_2.H_2O$ in 750 g of water. To the aqueous solution were added a solution in which 500 g of Cataloid Si-30 Water Glass (manufactured by Catalysts & Chemicals Ind. Co., Ltd.) is dissolved in 333 g of water, 177.5 g of 6% by mass of an aqueous NaOH solution, 317.6 g of 21.3% by mass of an aqueous tetrapropylammonium bromide solution and 15.0 g (corresponding to 10% by mass of a zeolite catalyst amount synthesized without adding a seed crystal) of an ammonium-type MFI structure zeolite (manufactured by Zeolyst International, Si/Al atomic ratio is 70) having an average particle size of 0.5 μm as a zeolite seed crystal under stirring to obtain an aqueous gel mixture.

Then, the aqueous gel mixture was placed in an autoclave of 3 L and the hydrothermal synthesis was carried out by stirring under the self pressure at 160° C. for 18 hours.

A white solid product obtained by the hydrothermal synthesis was filtered and washed with water, followed by drying at 120° C. for 5 hours and calcining at 520° C. for 10 hours in air. Then, the calcined product was soaked in 0.6 N hydrochloric acid, followed by stirring at room temperature for 24 hours to convert the type of the zeolite to a proton-type.

Thereafter, the product was filtered and washed with water and then dried at 120° C. for 5 hours, followed by calcining at 520° C. for 10 hours in air to obtain a proton-type zeolite catalyst B having the MFI structure and containing an alkaline earth metal.

Comparative Example 9

Figure 7:
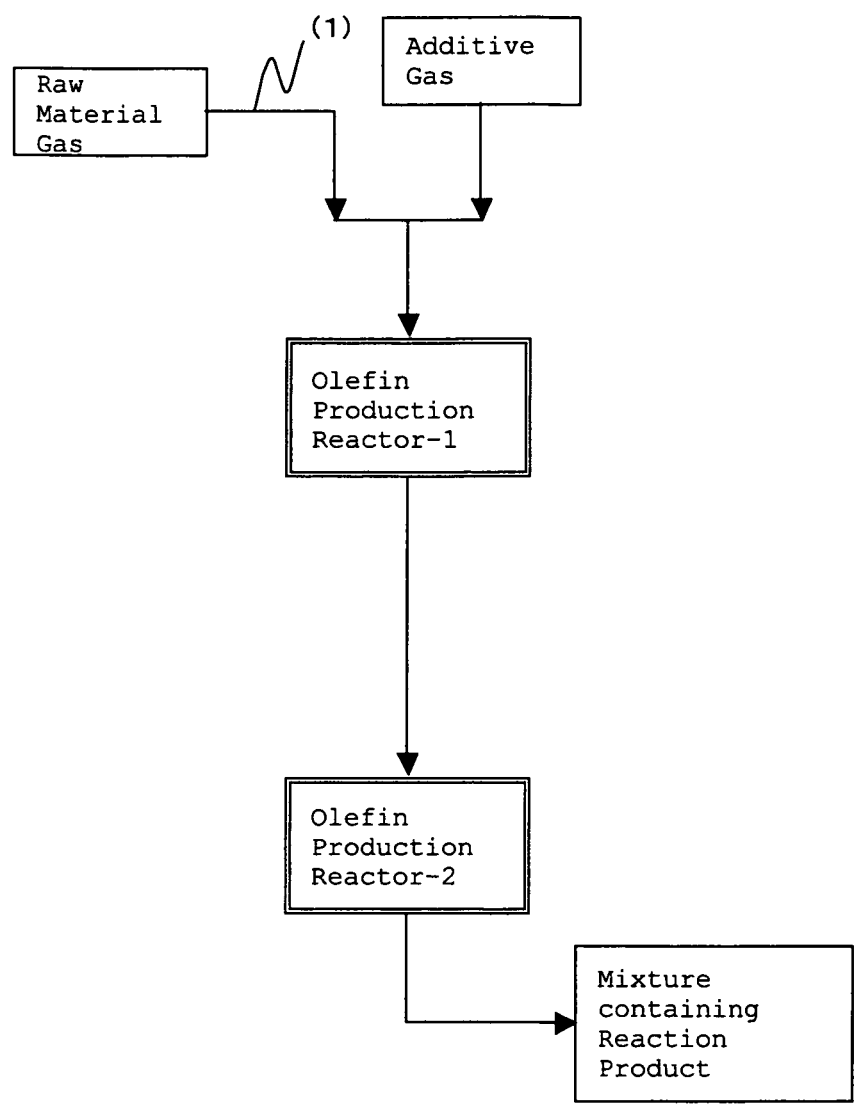
FIG. 7 shows an embodiment for producing lower olefins of Comparative Examples 9 and 11 and FIG. 8 shows an embodiment for producing lower olefins of Examples 3 to 9 and Comparative Examples 10 and 12.

The lower olefin production was carried out by using the equipment configuration shown in FIG. 7, in which two olefin synthesis reactors filled with the zeolite catalyst B obtained in Preparation Example 1 were connected in series. In addition, the olefin synthesis reactor-1 and the olefin synthesis reactor-2 were of the same scale and were provided with the same amount of the zeolite catalyst B.

Into the olefin synthesis reactor-1 was introduced the whole amount of a mixed gas consisting of dimethyl ether, methanol and steam as a feedstock gas and nitrogen as an additive gas in the feed gas composition shown in Table 2 under the conditions in which the space velocity (WHSV) on the basis of dimethyl ether was 0.42 h$^{-1}$. Into the olefin synthesis reactor-2 was introduced the whole amount of the reaction mixture obtained from the olefin synthesis reactor-1 at the exit temperature of 550° C., and a mixture containing reaction products was obtained. The exit temperature of the olefin synthesis reactor-2 was 550° C.

The resulting mixture containing the reaction products was analyzed by gas chromatography to determine the amount of the raw material and the content of propylene. As a result, it was found that a raw material, dimethyl ether and methanol, was not present in the mixture containing the reaction products and the conversion was 100%.

In addition, the time until the conversion is 99.9% was determined as the catalyst life by carrying out the reaction successively and continuously.

Example 3

Figure 8:
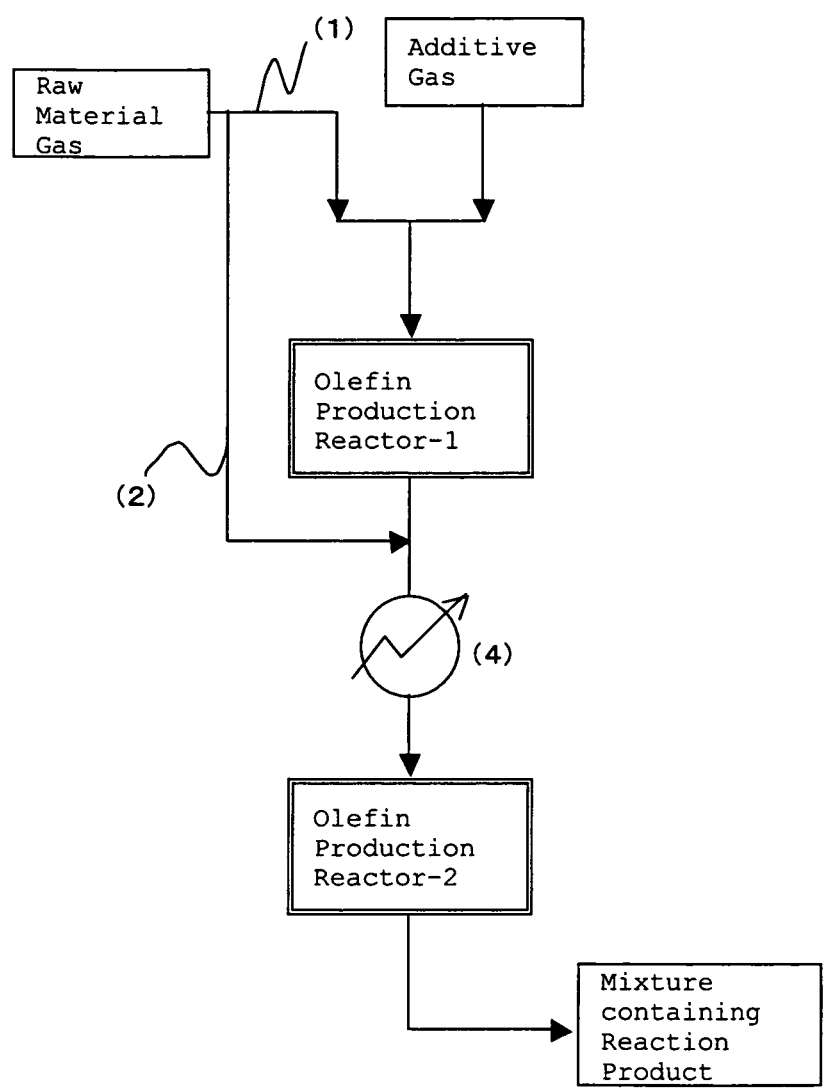

A feedstock gas was divided into 1:1 and introduced into the olefin synthesis reactor-1 and the olefin synthesis reactor-2 each by 50%. The lower olefin production was carried out by using the equipment configuration shown in FIG. 8, in which two olefin synthesis reactors filled with the zeolite catalyst B obtained in Preparation Example 1 are connected in series. The feed gas composition shown in Table 2 was used, and the additive gas was introduced only into the olefin synthesis reactor-1. The reaction was carried out by feeding the raw material into the system under the conditions in which the space velocity (WHSV) on the basis of dimethyl ether was 1.0 h$^{-1}$. In addition, the olefin synthesis reactor-1 and the olefin synthesis reactor-2 used were of the same scale and were provided with the same amount of the zeolite catalyst B, which is the same one as used in Comparative Example 9.

The reaction mixture obtained from the olefin synthesis reactor-1 at the exit temperature of 550° C. was cooled by a heat exchanger (4) and was introduced together with the divided feedstock gas into the olefin synthesis reactor-2. The exit temperature of the olefin synthesis reactor-2 was set at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

Example 4

In Example 3, the lower olefin production was carried out in a similar manner as in Example 3 except that the introduction rate of the feedstock gas was set at a space velocity (WHSV) of 4.0 h$^{-1}$ on the basis of dimethyl ether.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

Example 5

In Example 3, the lower olefin production was carried out in a similar manner as in Example 3 except that the introduction rate of the feedstock gas was set at a space velocity (WHSV) of 10.0 h$^{-1}$ on the basis of dimethyl ether.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

Example 6

In Example 3, the lower olefin production was carried out in a similar manner as in Example 3 except that the introduction rate of the feedstock gas was set at a space velocity (WHSV) of 30.0 h$^{-1}$ on the basis of dimethyl ether.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

Example 7

In Example 3, the lower olefin production was carried out in a similar manner as in Example 3 except that a gas containing nitrogen and isobutene at the ratio described in Table 2 was used as an additive gas. Here, the present Example using the additive gas containing isobutene is an experiment showing the effect in the case of using a recycled gas containing a $C_4$ olefin as an additive gas.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

Comparative Example 10

In Example 3, the lower olefin production was carried out in a similar manner as in Example 3 except that the introduction rate of the feedstock gas was set at a space velocity (WHSV) of 0.42 h$^{-1}$ on the basis of dimethyl ether.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

Comparative Example 11

In Comparative Example 9, the lower olefin production was carried out in a similar manner as in Comparative Example 9 except that the introduction rate of the feedstock gas was set at a space velocity (WHSV) of 1.0 h$^{-1}$ on the basis of dimethyl ether.

The exit temperature of the olefin synthesis reactor-1 was 550° C. and that of the olefin synthesis reactor-2 was 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set 100%, and shown in Table 2.

Comparative Example 12

In Example 3, the lower olefin production was carried out in a similar manner as in Example 3 except that the introduction rate of the feedstock gas was set at a space velocity (WHSV) of 75.0 h$^{-1}$ on the basis of dimethyl ether.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

Example 8

In Example 3, the lower olefin production was carried out in a similar manner as in Example 3 except that a gas consisting only of dimethyl ether was used as a feedstock gas and the composition of the feed gas was conditioned to be the ratio shown in Table 2.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as, in Comparative Example 9.

From the results obtained, the propylene yield and the catalyst life are, expressed in terms of relative values, respectively, to those of Comparative Example 9 set at 100%, and shown in Table 2.

Example 9

In Example 3, the lower olefin production was carried out in a similar manner as in Example 3 except that the composition of the feedstock gas shown in Table 2 was used and the composition of the feed gas was conditioned to be the ratio shown in Table 2.

The exit temperature of the olefin synthesis reactor-1 was set at 550° C. and that of the olefin synthesis reactor-2 at 550° C.

The mixture containing reaction products obtained from the olefin synthesis reactor-2 was analyzed in a similar manner as in Comparative Example 9. In addition, the catalyst life was determined in a similar manner as in Comparative Example 9.

From the results obtained, the propylene yield and the catalyst life are expressed in terms of relative values, respectively, to those of Comparative Example 9 set at 100%, and shown in Table 2.

TABLE 2

| | Example 3 | Example 4 | Example 5 | Example 6 | Example 7 | Comparative Example 9 | Comparative Example 10 | Comparative Example 11 | Comparative Example 12 | Example 8 | Example 9 |
|---|---|---|---|---|---|---|---|---|---|---|---|
| Divided feeding of a feedstock gas | With | With | With | With | With | Without | With | Without | With | With | With |
| WHSV (h$^{-1}$) | 1.0 | 4.0 | 10.0 | 30.0 | 1.0 | 0.42 | 0.42 | 1.0 | 75.0 | 1.0 | 1.0 |
| Composition of a feed gas (vol %) Feedstock gas | | | | | | | | | | | |
| Dimethyl ether | 12.75 | 12.75 | 12.75 | 12.75 | 12.75 | 12.75 | 12.75 | 12.75 | 12.75 | 15.00 | 12.75 |
| Methanol | 4.50 | 4.50 | 4.50 | 4.50 | 4.50 | 4.50 | 4.50 | 4.50 | 4.50 | 0.00 | 4.50 |

TABLE 2-continued

| | Example 3 | Example 4 | Example 5 | Example 6 | Example 7 | Comparative Example 9 | Comparative Example 10 | Comparative Example 11 | Comparative Example 12 | Example 8 | Example 9 |
|---|---|---|---|---|---|---|---|---|---|---|---|
| Steam ($H_2O$) Dilution gas | 12.75 | 12.75 | 12.75 | 12.75 | 12.75 | 12.75 | 12.75 | 12.75 | 12.75 | 0.00 | 50.00 |
| Nitrogen | 70.00 | 70.00 | 70.00 | 70.00 | 62.00 | 70.00 | 70.00 | 70.00 | 70.00 | 85.00 | 32.75 |
| Isobutene | 0.00 | 0.00 | 0.00 | 0.00 | 8.00 | 0.00 | 0.00 | 0.00 | 0.00 | 0.00 | 0.00 |
| Conversion (%) | 100.0 | 100.0 | 100.0 | 100.0 | 100.0 | 100.0 | 100.0 | 100.0 | 100.0 | 100.0 | 99.7 |
| Relative value of propylene yield (*1) when that of Comparative Example is 100% (%) | 131 | 148 | 148 | 148 | 240 | 100 | 104 | 115 | 148 | 134 | 139 |
| Relative value of a catalyst life (*2) when that of Comparative Example is 100% (%) | 42.0 | 10.5 | 4.2 | 1.4 | 59.3 | 100.0 | 100.0 | 42.0 | 0.6 | 26.7 | 0.0 (*3) |

(*1) The propylene yield to the feed amount of a raw material (the total of DME and methanol) in conversion to dimethyl ether (DME)
(*2) The time until the conversion is less than 99.9% is defined as the catalyst life.
(*3) DME was mixed in the product from the start of the reaction.

The following matters were confirmed from the results of Examples 3 to 9 and Comparative Examples 9 to 12 shown in Table 2.

1. From a comparison of Comparative Example 9 with Comparison Example 11, it was found that the propylene yield was increased by increasing the WHSV from 0.42 $h^{-1}$ to 1.0 $h^{-1}$ and the increase in the WHSV was effective for the improvement in the propylene yield.

2. From a comparison of Comparative Example 9 with Comparative Example 10, it was found that there was almost no increase in the propylene yield even by collectively feeding the feedstock gas only into the most upstream olefin synthesis reactor and even by dividing and feeding the feedstock gas into individual reactors connected in series under the condition of a WHSV of 0.42 $h^{-1}$.

3. From a comparison of Example 3 with Comparative Example 11, it was found that the propylene yield was substantially increased by dividing and feeding the feedstock gas into individual reactors connected in series under the condition of a WHSV of 1.0 $h^{-1}$, as compared with the case of collectively feeding the feedstock gas only into the most upstream olefin synthesis reactor.

4. From the results of Comparative Example 10 and Examples 3 and 4, it was found that the propylene yield was increased with the increase of a WHSV in a range of a WHSV of 4.0 $h^{-1}$ or less, even in the case of dividing and feeding the raw material under the conditions of the present Examples and Comparative Examples.

From the results of Examples 5 and 6, Comparative Examples 10 and 12 and Examples 3 and 4, it was found that, although the propylene yield was not increased with the increase in the WHSV in a range of a WHSV of 4.0 $h^{-1}$ or more, a higher propylene yield was maintained, as compared with the case of a WHSV of 4.0 $h^{-1}$ or less. However, from the results of Comparative Example 12, it was found that, if the WHSV was larger than 50 $h^{-1}$, the catalyst life became very short and the operating conditions were not industrially acceptable.

6. From the results of Examples 3 and 8, it was found that, although the propylene yield was comparable when the steam concentration in the feed gas was 5% by volume or more and when that was less than 5% by volume, the catalyst life was longer when the steam concentration was 5% by volume or more.

7. From the results of Example 3 and Example 9, it was found that, although the propylene yield was comparable when the steam concentration in the feed gas was more than 30% by volume and when that was 30% by volume or less, the conversion was insufficient from the start in the case of Example 9 in which the steam concentration was larger than 30% by volume. This seems to be caused by the reason that the acid sites of the catalyst were covered partially and the acid density was reduced when the steam concentration was extremely high.

8. From the results of Examples 3 and 7, it was found that the propylene yield was substantially increased and the catalyst life was extended in the case (Example 7) where isobutene was contained in an additive gas, which is a model case of using a gas containing $C_4$ and $C_5$ olefins as a recycled gas.

From the above results, it has been confirmed that the method for producing lower olefins of the present invention is an excellent practical method that can produce lower olefins with a high yield in a simple and easy way.

The present invention is useful as a method for producing lower olefins capable of suppressing the deactivation of a zeolite catalyst and also effectively suppressing the deactivation of a regenerated zeolite catalyst. In addition, the present invention is industrially useful as a method for effectively producing lower olefins from a raw material containing dimethyl ether and with a high yield of propylene.

The invention claimed is:

1. A method for producing lower olefins comprising:

introducing a feed gas, which is composed of a feedstock gas containing dimethyl ether and an additive gas containing steam in which the ratio of steam in the total amount of feed gas is 5 to 30% by volume, into an olefin synthesis reactor, bringing the feedstock gas into contact with a zeolite catalyst in the reactor to produce a hydrocarbon product containing $C_2$-$C_5$ olefins, separating and recovering propylene from the hydrocarbon product, and using at least a part of the remainder after the separation as at least a part of the additive gas, wherein said method comprises multiple reactors connected in parallel, or connected in a combination of series and parallel, wherein the additive gas contains $C_4$ and/or $C_5$ olefins derived from the remainder after separating propylene from the hydrocarbon product, the ratio of the total amount of the $C_4$ and/or $C_5$ olefins in the additive gas to the total amount of methanol and dimethyl ether in the feedstock gas is 0.3 to 5.0 by molar ratio on a carbon basis, and the ratio of an additive gas excluding steam to the feedstock gas introduced into the olefin synthesis reactor (the number of moles of the additive gas excluding steam:the number of moles of the feedstock gas on a carbon basis) is in the range of 0.2 to 5.0.

2. The method for producing lower olefins according to claim 1, wherein the feedstock gas is a gas containing dimethyl ether and methanol.

3. The method for producing lower olefins according to claim 1, wherein the molar fraction of dimethyl ether and methanol (dimethyl ether:methanol) in the feedstock gas is in the range of 6:0 to 6:5.

4. The method for producing lower olefins according to claim 1, wherein the zeolite catalyst has an MFI structure.

5. The method for producing lower olefins according to claim 1, wherein the atomic ratio of silicon to aluminum (Si/Al) in the zeolite catalyst is in the range of 50 to 300 by molar ratio.

6. The method for producing lower olefins according to claim 1, wherein the zeolite catalyst contains an alkaline earth metal M and the atomic ratio of the alkaline earth metal M to aluminum (M/Al) in the zeolite catalyst is 0.5 or more by molar ratio.

* * * * *

UNITED STATES PATENT AND TRADEMARK OFFICE
CERTIFICATE OF CORRECTION

PATENT NO.         : 8,530,714 B2                                            Page 1 of 1
APPLICATION NO.    : 12/085055
DATED              : September 10, 2013
INVENTOR(S)        : Hirofumi Ito It is certified that error appears in the above-identified patent and that said Letters Patent is hereby corrected as shown below:

Title Page, Column 2, Item (57) Abstract, Line 16, delete "C2-C5" and insert -- $C_2$-$C_5$ --

Signed and Sealed this
Twenty-second Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,530,714 B2                                    Page 1 of 1
APPLICATION NO.  : 12/085055
DATED            : September 10, 2013
INVENTOR(S)      : Ito et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 988 days.

Signed and Sealed this

Fifteenth Day of September, 2015

Michelle K. Lee
*Director of the United States Patent and Trademark Office*